United States Patent
Park et al.

(10) Patent No.: US 7,854,316 B2
(45) Date of Patent: Dec. 21, 2010

(54) DENTAL IMPLANT PACKAGE

(75) Inventors: Kwang Bum Park, Daegu (KR);
Kyoung Ho Ryoo, Gwanju (KR); Seok Kyu Choi, Busan (KR); Hae Yong Lee, Gyeongsan-si (KR)

(73) Assignee: Megagen Implant Co., Ltd. (KR)

( * ) Notice: Subject to any disclaimer, the term of this patent is extended or adjusted under 35 U.S.C. 154(b) by 30 days.

(21) Appl. No.: 12/441,861

(22) PCT Filed: Dec. 13, 2006

(86) PCT No.: PCT/KR2006/005434
§ 371 (c)(1),
(2), (4) Date: Jul. 20, 2009

(87) PCT Pub. No.: WO2008/047976
PCT Pub. Date: Apr. 24, 2008

(65) Prior Publication Data
US 2010/0065443 A1      Mar. 18, 2010

(30) Foreign Application Priority Data
Oct. 19, 2006      (KR) ..................... 10-2006-0101677

(51) Int. Cl.
*A61B 19/02*      (2006.01)
(52) U.S. Cl. .................. 206/63.5; 206/369; 433/174
(58) Field of Classification Search ............... 206/63.5, 206/368, 369, 438, 570; 433/172–176
See application file for complete search history.

(56) References Cited

U.S. PATENT DOCUMENTS

| | | | |
|---|---|---|---|
| 5,062,800 A * | 11/1991 | Niznick ..................... 433/173 |
| 5,368,160 A * | 11/1994 | Leuschen et al. ........... 206/63.5 |
| 5,558,230 A | 9/1996 | Fischer et al. |
| 5,622,500 A * | 4/1997 | Niznick ..................... 433/173 |
| 5,961,330 A | 10/1999 | Hanson |
| 6,247,932 B1 * | 6/2001 | Sutter ........................ 433/173 |
| 6,595,352 B2 * | 7/2003 | Bleuer ...................... 206/63.5 |
| 6,913,465 B2 | 7/2005 | Howlett et al. |
| 6,955,258 B2 * | 10/2005 | Howlett et al. ............. 206/63.5 |
| 2001/0015326 A1 * | 8/2001 | Bleuer ...................... 206/63.5 |
| 2003/0221977 A1 * | 12/2003 | Kumar et al. .............. 206/63.5 |
| 2005/0023166 A1 * | 2/2005 | Howlett et al. .............. 206/369 |

OTHER PUBLICATIONS

International Search Report-PCT/KR2006/005434 dated Jul. 16, 2007.
Written Opinion-PCT/KR2006/005434 dated Jul. 16, 2007.

* cited by examiner

*Primary Examiner*—Luan K Bui
(74) *Attorney, Agent, or Firm*—Cantor Colburn LLP (57) ABSTRACT

A dental implant package includes a main body having a partition portion that is formed therein and separates a fixture accommodation space accommodating a fixture of a dental implant from an auxiliary accommodation space accommodating any of a healing abutment and a cover screw, wherein a first opening and a second opening are formed at both ends of the main body, a leveler accommodated in at least a part of the fixture accommodation space and supporting the fixture accommodated in the fixture accommodation space at a predetermined height, a first cover detachably coupled to the main body and blocking the first opening, and a second cover detachably coupled to the main body and blocking the second opening. The fixture and any of the healing abutment and the cover screw can be stored with a simple structure. Also, the fixture and the healing abutment or the cover screw can be easily pulled out during an implant operation.

15 Claims, 5 Drawing Sheets

DENTAL IMPLANT PACKAGE

TECHNICAL FIELD

The present invention relates to a dental implant package, and more particularly, to a dental implant package capable of storing a fixture and any of a cover screw and a healing abutment together and facilitating easy putting in and pulling out the stored part.

BACKGROUND ART

The word "Implant" originally signifies a replacement to recover damaged or lost human tissues. For the specific field of a dentistry, the implant signifies transplantation of an artificial tooth. That is, the implant is an operation to recover the function of a tooth by placing a dental root made of titanium that shows no rejection symptoms to a human body to replace a lost dental root, in an alveolar bone where a tooth is removed, and fixing an artificial tooth.

In the case of a general dental prosthesis or denture, surrounding teeth and bones are damaged as time passes. In contrast, the implant does not damage surrounding tooth tissues and causes no decayed tooth while providing the same function and shape as a natural tooth. Thus, the implant can be used semi-permanently.

Also, the implant improves not only the restoration of a single lost tooth but also the function of the artificial teeth of partially toothless or completely toothless patients and enhances the aesthetic feature in the restoration of dental prosthesis. Furthermore, the implant can distribute excessive stress applied to the tissues of the surrounding support bone so as to help the stabilization of a row of teeth.

Although the implant is variously used to signify a transplanted artificial tooth, an artificial tooth operation, or a fixture (an artificial tooth root) needed for the artificial tooth operation, in the present specification, the implant is limitedly used to signify a fixture used for an artificial tooth operation.

The implant is generally stored in an antibiotic sealed package. This is to prevent the contamination of an implant placed in an alveolar bone, that is, a fixture, by external foreign materials or germs.

According to a conventional dental implant package, an implant is accommodated in an inner container and an inner cover is coupled to the inner container. The inner container with the inner cover is accommodated in an outer container and an outer cover is coupled to the outer container so that the implant is packed.

Also, another conventional dental implant package has been suggested in which a part such as a healing abutment is coupled to an upper end portion of an implant, an inner cover and an inner container are coupled to each other with the part such as a healing abutment fixed to the inner cover, the inner cover and the inner container accommodate in an outer container, and the outer cover is coupled to the outer container.

However, in the conventional dental implant packages, it is not easy to open the package and pull out the implant for an implant operation due to a dual structure of the package so that an implant operator feels inconvenience.

DISCLOSURE OF INVENTION

Technical Problem

To solve the above and/or other problems, the present invention provides a dental implant package which can not only store a fixture and any of a healing abutment and a cover screw in a simple structure but also facilitate easy pulling out of the fixture and the healing abutment or cover screw for an implant operation.

ADVANTAGEOUS EFFECTS

According to the present invention, not only a fixture and any one of a healing abutment and a cover screw can be stored in a simple structure, but also the fixture and the healing abutment or cover screw can be easily pulled out for an implant operation.

BEST MODE FOR CARRYING OUT THE INVENTION

According to an aspect of the present invention, a dental implant package comprises a main body having a partition portion that is formed therein and separates a fixture accommodation space accommodating a fixture of a dental implant from an auxiliary accommodation space accommodating any of a healing abutment and a cover screw, wherein a first opening and a second opening are formed at both ends of the main body, a leveler accommodated in at least a part of the fixture accommodation space and supporting the fixture accommodated in the fixture accommodation space at a predetermined height, a first cover detachably coupled to the main body and blocking the first opening, and a second cover detachably coupled to the main body and blocking the second opening.

An accommodation protrusion protruding from a lower surface in a lower end of the leveler and an accommodation hole to which the accommodation protrusion is forcibly coupled is formed at a side of the partition portion facing the leveler.

An insertion accommodation hole in which any of the healing abutment and the cover screw is at least partially inserted is formed at the partition portion toward the auxiliary accommodation space.

The insertion accommodation hole is formed by a hollow cylinder provided by extending from the partition portion and the accommodation hole and the insertion accommodation hole are connected to each other.

The leveler has a cylindrical shape having an open upper end portion and a leveler cover formed of a titanium material is coupled to the upper end portion of the leveler.

The dental implant package further comprises a protection ring formed of a titanium material and coupled to an end portion of the main body forming the first opening.

A push protrusion protruding from an outer circumferential wall of the first cover in a radial direction is provided at the first cover.

A fixture push portion pushing the fixture when the fixture is coupled to the main body is provided on an upper surface of an inner wall of the first cover.

A push uneven portion having an uneven shape is formed at least a part of an outer circumferential wall of the second cover.

According to an aspect of the present invention, a dental implant package comprises a main body having a partition portion that is formed therein and separates a fixture accommodation space accommodating a fixture of a dental implant from an auxiliary accommodation space accommodating any of a healing abutment and a cover screw, wherein a first opening and a second opening are formed at both ends of the main body, a fixture holder accommodated in at least a part of the fixture accommodation space and supporting the fixture accommodated in the fixture accommodation space, a first cover detachably coupled to the main body and blocking the first opening, and a second cover detachably coupled to the main body and blocking the second opening.

The fixture holder comprises a hollow cylinder portion having a hollow shape, an arc support portion having an arc sectional shape and extending upwardly from the hollow cylinder portion, and a grip portion coupled to an inner circumferential wall of the arc support portion and gripping the fixture inserted and accommodated in the arc support portion.

An insertion accommodation hole in which any of the healing abutment and the cover screw is at least partially inserted is formed at the partition portion toward the auxiliary accommodation space.

The insertion accommodation hole is formed by a hollow cylinder provided by extending from the partition portion and the accommodation hole and the insertion accommodation hole are connected to each other.

A push protrusion protruding from an outer circumferential wall of the first cover in a radial direction is provided at the first cover.

A push uneven portion having an uneven shape is formed at least a part of an outer circumferential wall of the second cover.

MODE FOR INVENTION

The attached drawings for illustrating preferred embodiments of the present invention are referred to in order to gain a sufficient understanding of the present invention, the merits thereof, and the objectives accomplished by the implementation of the present invention.

Hereinafter, the present invention will be described in detail by explaining preferred embodiments of the invention with reference to the attached drawings. Like reference numerals in the drawings denote like elements.

Figure 1:
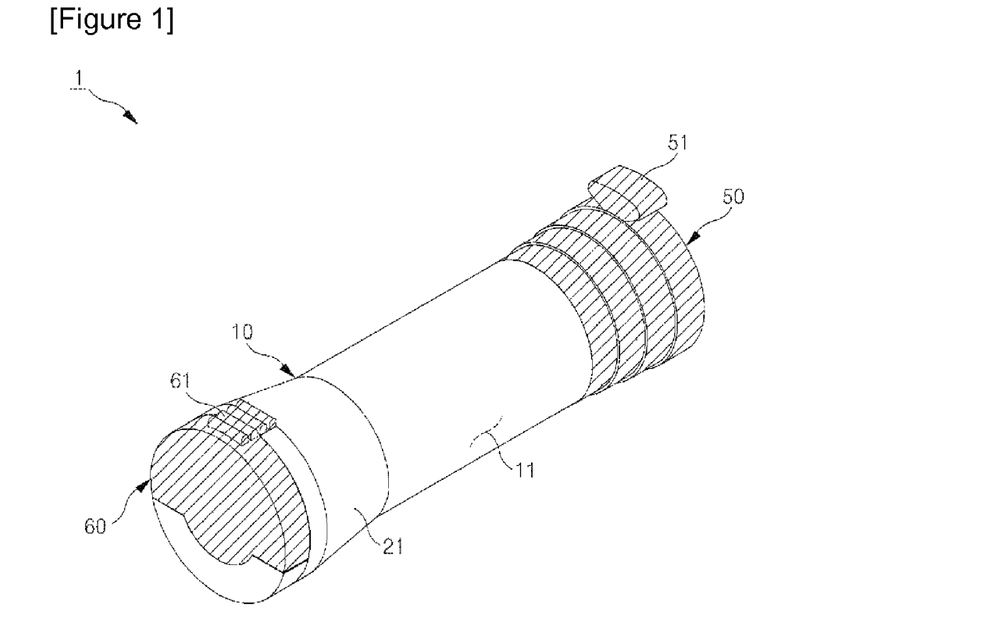
FIG. 1 is a perspective view of a dental implant package according to an embodiment of the present invention.
Figure 2:
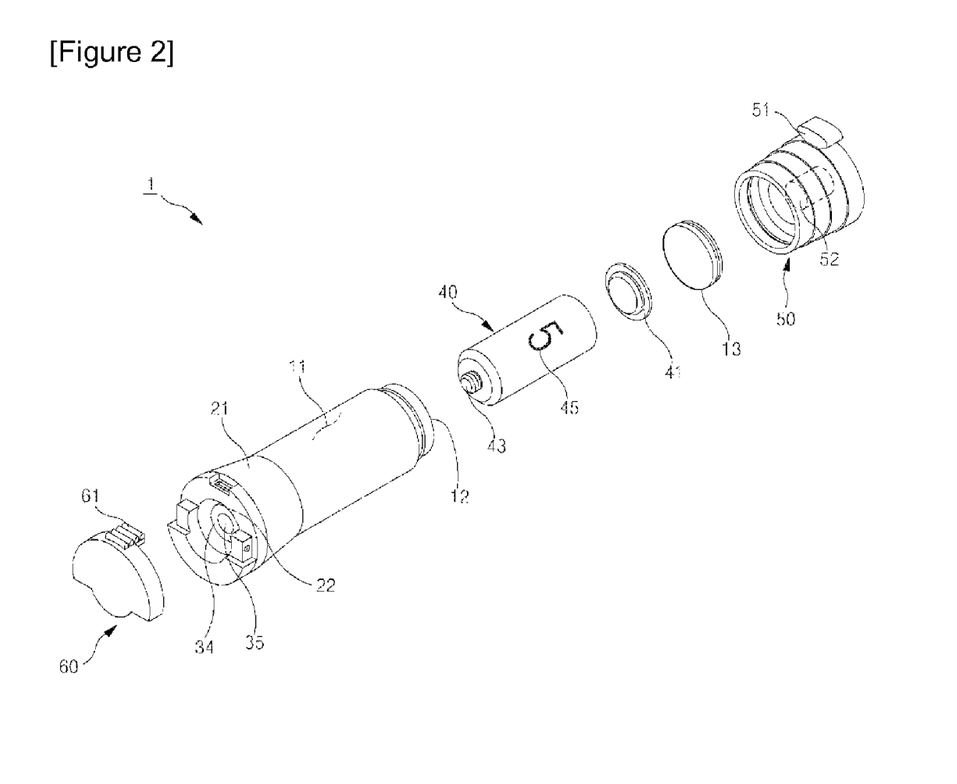
FIG. 2 is an exploded perspective view of the dental implant package of FIG. 1.
Figure 3:
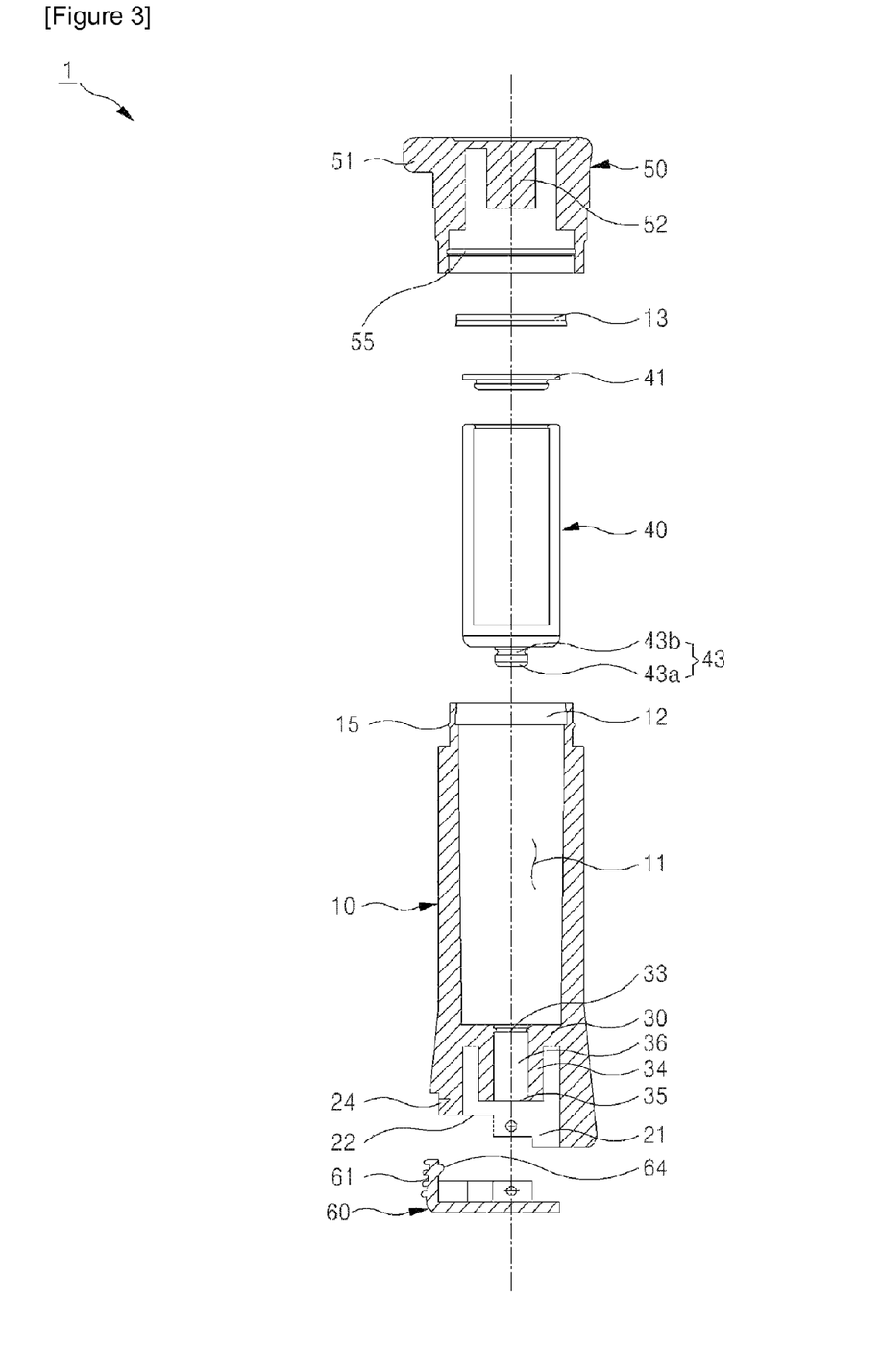
FIG. 3 is a sectional view of the dental implant package of FIG. 2.
Figure 4:
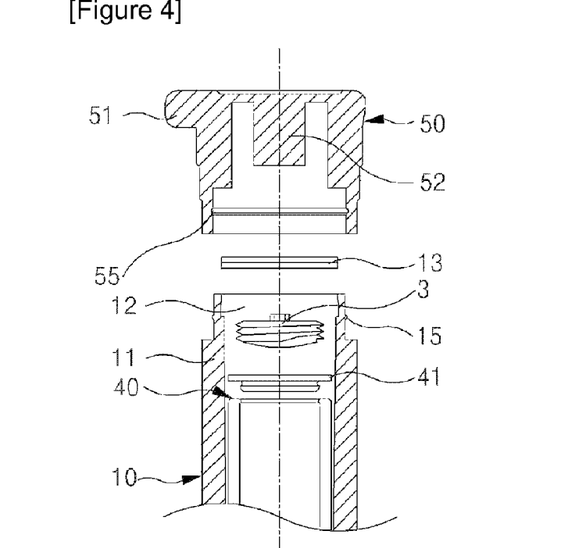
FIG. 4 illustrates a state where a fixture is accommodated in a fixture accommodation space of FIG. 3.
Figure 5:
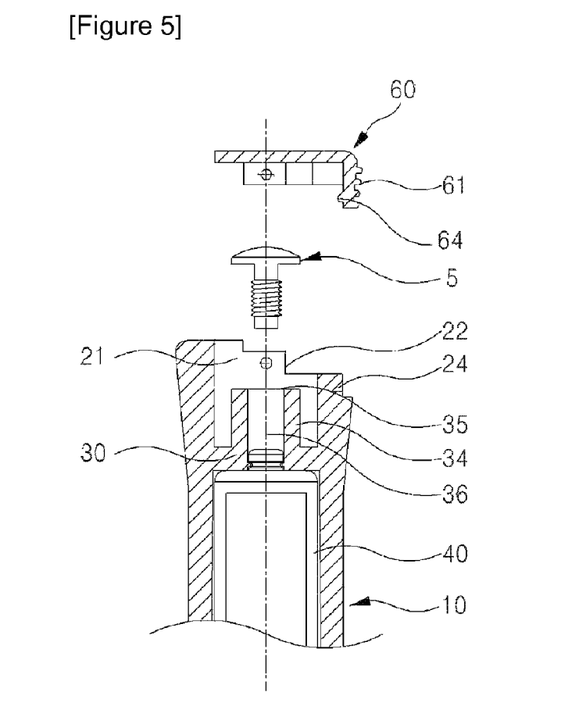
FIG. 5 illustrates a state where a cover screw is accommodated in an auxiliary accommodation space of FIG. 3.

FIG. 1 is a perspective view of a dental implant package according to an embodiment of the present invention. FIG. 2 is an exploded perspective view of the dental implant package of FIG. 1. FIG. 3 is a sectional view of the dental implant package of FIG. 2. FIG. 4 illustrates a state where a fixture is accommodated in a fixture accommodation space of FIG. 3. FIG. 5 illustrates a state where a cover screw is accommodated in an auxiliary accommodation space of FIG. 3.

As shown in the above drawings, a dental implant package 1 according to an embodiment of the present invention includes a main body 10 having a cylindrical shape having a fixture accommodation space 11 for accommodating a fixture 3 and an auxiliary accommodation space 21 for accommodating a cover screw 5 or a healing abutment (not shown), a leveler 40 detachably accommodated in the fixture accommodation space 11 in a state of supporting a fixture 3, a first cover 50 detachably coupled to the main body 10 and blocking a first opening 12 formed at an end of the main body 10, and a second cover 60 detachably coupled to the main body 10 and blocking a second opening 22 formed at the other end of the main body 10. Although the cover screw 5 or the healing abutment can be accommodated in the auxiliary accommodation space 21, in the present embodiment, the cover screw 5 is accommodated.

The main body 10 is an ampule body manufactured of transparent or translucent plastic to check a product existing inside the main body 10 from the outside. In the main body 10, a partition portion 30 separates a fixture accommodation space 11 for accommodating the fixture 3 and the auxiliary accommodation space 21 for accommodating the cover screw 5.

The partition portion 30 includes an accommodation hole 33 formed in a surface of the partition portion 30 facing the fixture accommodation space 11, to which the leveler 40 is coupled and supported, an insertion accommodation hole 35 provided in the central area of a hollow cylinder 34 that is formed at the other surface of the partition portion 30 facing the auxiliary accommodation space 21 to accommodate and store the cover screw 5, and a connection hole 36 connecting the accommodation hole 33 and the insertion accommodation hole 35. These elements will be described below with other elements.

The leveler 40 has a cylindrical shape to be inserted in the fixture accommodation space 11 of the main body 10 and includes an open upper end portion to which a leveler cover 41 is coupled. The leveler 40 can have a different shape according to the diameter and length of the fixture 3. Accordingly, an operator can recognize the type of the fixture 3 stored in the fixture accommodation space 11 through a numeric letter 45 indicated on the outer surface of the leveler 40. In the present embodiment, the leveler 40 is appropriate for supporting a fixture that belongs to one having a relatively large diameter and a short length. For example, when a fixture (not shown) that is longer than the fixture 3 of the present embodiment is stored in the fixture accommodation space 11, a leveler (not shown) having a length shorter than that of the leveler 40 of the present embodiment is used.

An accommodation protrusion 43 protrudes from the lower surface of a lower end portion of the leveler 40. As the accommodation protrusion 43 is forcibly inserted in the accommodation hole 33 of the partition portion 30, the leveler 40 can be stably stored in the fixture accommodation space 11 without movements. In the shape of the accommodation protrusion 43, as shown in FIG. 3, a lower portion 43a of the accommodation protrusion 43 is more convex than an upper portion 43b thereof. Since the accommodation hole 33 has a shape corresponding to the shape of the accommodation protrusion 43, the accommodation protrusion 43 is coupled to the accommodation hole 33. Thus, the leveler 40 can be appropriately supported in the fixture accommodation space 11.

The leveler cover 41 is manufactured of a titanium material and directly supports the fixture 3 that is stored in the fixture accommodation space 11. The leveler cover 41 is appropriate for supporting the fixture 3 that is manufactured of a titanium material and appropriately coupled to the opening of the leveler 40. The reason for manufacturing the leveler cover 41 using a titanium material is to prevent the change of the characteristic of the fixture 3 made of the titanium material during which the fixture 3 is stored in the fixture accommodation space 11.

For example, when the fixture 3 is manufactured of a different material, for example, plastic, and stored in a separate accommodation portion (not shown), the characteristic of a screw portion of the fixture 3 made of a titanium material can be changed as it contacts a plastic accommodation portion so that the state of a gum can be contaminated or a side effect can be generated during an implant operation. Thus, to prevent these problems, the leveler cover 41 is manufactured of a titanium material that is substantially the same as the material of the fixture 3.

A protection ring 13 made of a titanium material is coupled to an opening portion of the fixture accommodation space 11, that is, the area of the main body 10 forming the first opening 12, to prevent the upper portion of the fixture 3 from directly contacting the main body 10 that is made of plastic. Accordingly, as the protection ring 13 made of a titanium material directly contacts the outer circumferential portion of the upper portion of the fixture 3, the change of the characteristic of the fixture 3 by a material having a different physical characteristic, for example, plastic, can be prevented. Further, as the outer diameter of the upper portion of the fixture 3 does almost match the inner diameter of the protection ring 13, the fixture 3 can be supported in the fixture accommodation space 11.

A first cover 50 is coupled to the area of the main body 10 where the first opening 12 of the fixture accommodation space 11 is formed and blocks the first opening 12 to prevent the escape of the fixture 3 stored in the fixture accommodation space 11 and the contact of external foreign materials with the fixture 3.

The first cover 50 is detachably coupled to the area of the main body 10 for forming the first opening 12 so that the fixture 3 can be easily pulled out from the fixture accommodation space 11. As shown in FIG. 4, the end portion of the fixture accommodation space 11 of the main body 10 has an outer diameter smaller than that of the middle area of the main body 10 so that the first cover 50 can be detachably coupled to the first opening 12 of the fixture accommodation space 11 of the main body 10. Also, a protruding portion 15 protrudes from the outer surface of the main body 10 for forming the first opening 12 in the circumferential direction. A groove portion 55 corresponding to the protruding portion 15 of the main body 10 is provided on the inner surface of the first cover 50 in the circumferential direction. Thus, the first cover 50 is forcibly coupled to the protruding portion 15 of the main body 10 for forming the first opening 12. As a result, a slight amount of a force is needed to separate the first cover 50 from the main body 10.

To this end, a push protrusion 51 protruding from the outer circumferential wall of the first cover 50 in the radial direction is provided on the first cover 50. By pushing the push protrusion 51 with a slight amount of a force, the first cover 50 can be easily separated from the main body 10.

Also, a fixture push portion 52 for maintaining the position of the fixture 3 by pressing the fixture 3 stored in the leveler 40 accommodated in the fixture accommodation space 11 at a predetermined pressure when being coupled to the main body 10 is provided on an upper surface of the inner wall of the first cover 50. The fixture push portion 52 makes the fixture 3 stored at a predetermined position in the fixture accommodation space 11 without movements.

Thus, as shown in FIG. 4, the fixture 3 can be stored in the fixture accommodation space 11 by being appropriately supported by the leveler 40 having the leveler cover 41 coupled to the upper surface thereof, the protection ring 13, and the fixture push portion 52 of the first cover 50.

As mentioned above, in the main body 10, in addition to the fixture accommodation space 11 for accommodating the fixture 3, the auxiliary accommodation space 21 is provided to auxiliarily accommodate the cover screw 5 coupled to a female screw portion (not shown) formed in the upper portion of the fixture 3. In the present embodiment, the cover screw 5 is accommodated in the auxiliary accommodation space 21. However, if necessary, a healing abutment (not shown) coupled to the female screw portion formed on the upper surface of the fixture 3 and maintained for a period during which the fixture 3 is osseointegrated in an alveolar bone. Also, other auxiliary parts can be accommodated in the auxiliary accommodation space 21.

The insertion accommodation hole 35 in which a male screw portion of the cover screw 5 screw coupled to a portion of the cover screw 5, that is, the female screw portion of the fixture 3, is inserted, is provided in the auxiliary accommodation space 21. The insertion accommodation hole 35 is provided in the hollow cylinder 34 extending from the partition portion 30 toward the auxiliary accommodation space 21. Since the cover screw 5 is not a factor that is directly transplanted in the alveolar bone, the cover screw 5 does not need to be supported by the accommodation portion of a titanium material. Accordingly, the cover screw 5 can be kept by being partially inserted in the insertion accommodation hole 35.

The second cover 60 is coupled to an end portion of the main body 10 at the side of the auxiliary accommodation space 21, that is, the area of the main body 10 for forming the second opening 22, to prevent the escape of the cover screw 5 from the insertion accommodation hole 35. A push uneven portion 61 is formed at the outer wall of the second cover 60 so that the second cover 60 can be easily installed on and detached from the second opening 22.

A coupling portion is formed at each of the inner surface of the second cover 60 and the outer surface of the area of the main body 10 for forming the second opening 22, to correspond to each other. In particular, a protruding portion 64 is formed on the inner side of the second cover 60 where the push uneven portion 61 is formed and a catch groove 24 corresponding to the protruding portion 64 is formed in the outer surface of the area of the main body 10 for forming the second opening 12 so that the protruding portion 64 and the catch groove 24 can be stably coupled to each other. Also, when a user pushes using a hand the push uneven portion 61 formed on the outer wall, the second cover 60 can be easily separated from the main body 10.

The connection hole 36 connecting the insertion accommodation hole 35 at the side of the auxiliary accommodation space 21 and the accommodation hole 33 at the side of the fixture accommodation space 11 is formed at the central area of the partition portion 30 that separates the fixture accommodation space 11 and the auxiliary accommodation space 21. When the accommodation protrusion 43 of the leveler 40 is over-forcibly coupled to the accommodation hole 33 of the partition portion 30 in the fixture accommodation space 11 so that the leveler 40 cannot be separated from the fixture accommodation space 11, or the cover screw 5 is forcible coupled to the insertion accommodation hole 35 so that the separation of the cover screw 5 is not easy, the leveler 40 or the cover screw 5 can be easily separated by pushing the leveler 40 or the cover screw 5 using a tool such as a gimlet from the opposite side.

For example, when the accommodation protrusion 43 of the leveler 40 is forcibly coupled to the accommodation hole 33 of the partition portion 30 and difficult to be separated from the accommodation hole 33, the leveler 40 can be easily separated from the accommodation hole 33 by pushing the accommodation protrusion 33 using a tool such as a gimlet through the connection hole 36 from the auxiliary accommodation space 21.

The assembly method of a dental implant package configured as above according to an embodiment of the present invention and the storing and pulling out operations of the fixture and the cover screw will be described below.

First, to store the fixture 3 in the fixture accommodation space 11 in the main body 10 of the dental implant package 1, the first cover 50 blocking the first opening 12 formed at the end portion of the main body 10 is separated. The first cover 50 blocking the first opening 12 can be easily separated by pushing the push protrusion 51 provided on the outer wall of the first cover 50. Next, the leveler 40 suitable for the shape of the fixture 3 is selected using a numeric letter 45 (please refer to FIG. 2) indicated on the outer surface of the leveler 40. Then, the level cover 41 formed of a titanium material is coupled to the upper portion of the leveler 40.

After the leveler cover 41 is coupled, the leveler 40 is put into the fixture accommodation space 11. Since the accommodation protrusion 43 formed on the lower surface of the leveler 40 is forcibly coupled to the accommodation hole 33 formed on the partition portion 30, the leveler 40 can be firmly supported in the fixture accommodation space 11. The protection ring 13 is coupled to the upper area of the fixture accommodation space 11, that is, the inside of the area of the main body 10 for forming the first opening 12. Since the protection ring 13 is also formed of a titanium material like the leveler cover 41, the change of the characteristic of the fixture 3 during which the fixture 3 is stored in the dental implant package 1 can be prevented.

Next, the fixture 3 is inserted in the fixture accommodation space 11 to be supported on the upper surface of the leveler cover 41. Since the fixture push portion 52 protrudes from the upper surface of the inner wall of the first cover 50, when the first cover 50 is coupled to the main body 10, the fixture push portion 52 presses the upper end portion of the fixture 3 so that the fixture 3 can be stably stored. Since the operation of pulling out the fixture 3 stored in the fixture accommodation space 11 is the opposite to the above-described insertion operation, a description thereof will be omitted herein.

Meanwhile, to accommodate the cover screw 5 in the auxiliary accommodation space 21, the second cover 60 blocking the second opening 22 is separated from the main body 10. Since the push uneven portion 61 is provided at the outer wall of the second cover, the second cover 60 can be easily separated from the area of the main body 10 for forming the second opening 22.

Next, after inserting the cover screw 5 in the insertion accommodation hole 35 of the hollow cylinder 34 provided in the auxiliary accommodation space 21, the second cover 60 is coupled to the main body 10 so that the cover screw 5 is completely accommodated in the auxiliary accommodation space 21. Since the operation of pulling out the cover screw 5 from the auxiliary accommodation space 21 is the opposite to the above-described insertion operation, a description thereof will be omitted herein.

The dental implant package 1 according to the present embodiment can not only prevent intrusion of external foreign materials and germs but also store the fixture 3 and the cover screw 5 or the healing abutment at the same time in a single dental implant package. Also, since the fixture 3 made of a titanium material contacts only the leveler cover 41 and the protection ring 13 that are made of a titanium material, the change of the characteristic of the fixture 3 can be prevented.

Figure 6:
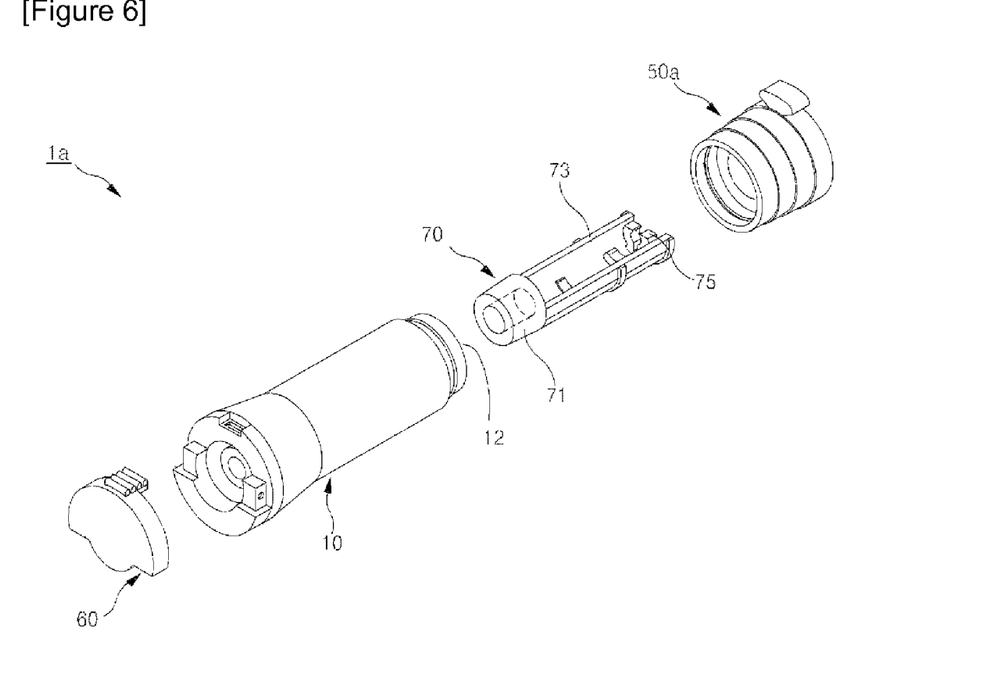
FIG. 6 is an exploded perspective view of a dental implant package according to another embodiment of the present invention.
Figure 7:
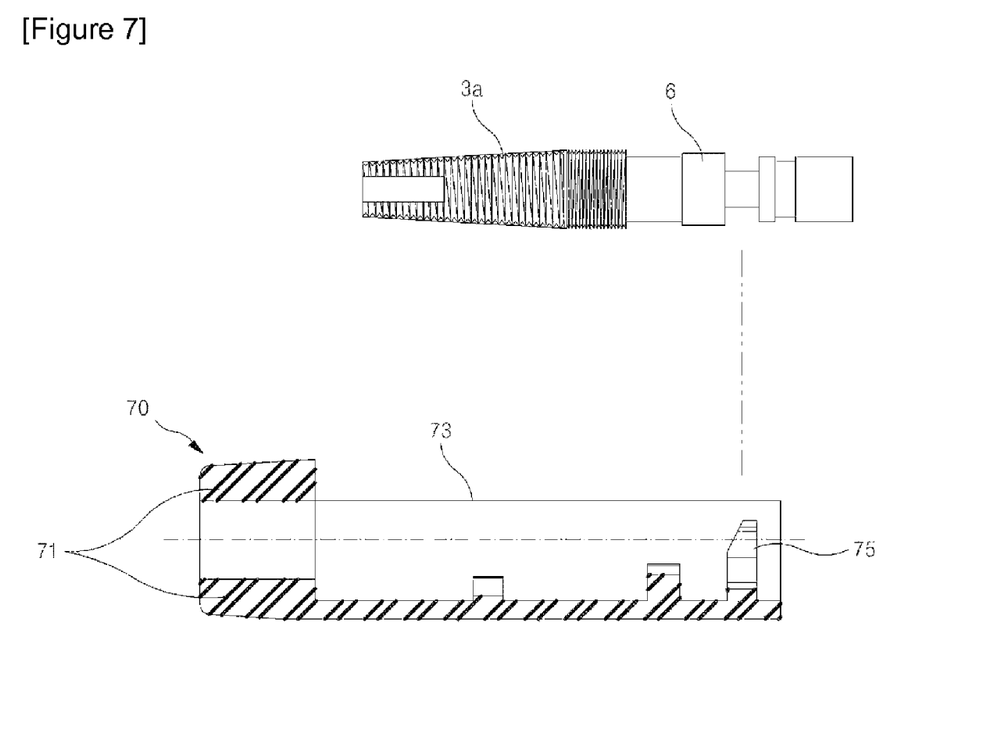
FIG. 7 is a sectional view for explaining that a fixture where a mount is installed is coupled to a fixture holder of FIG. 6.
Figure 8:
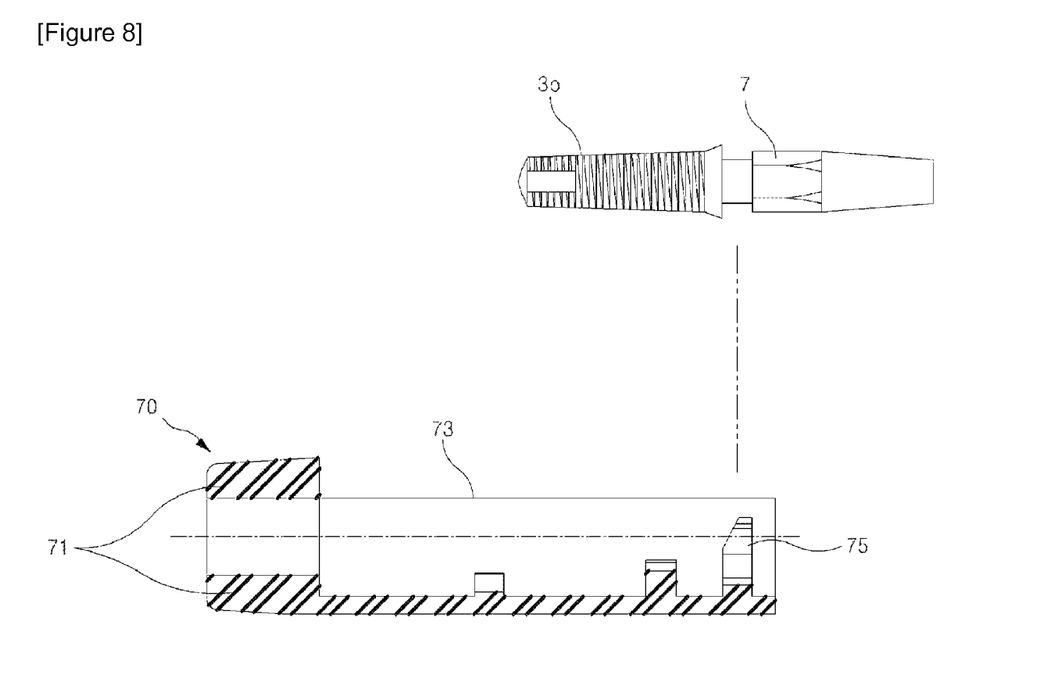
FIG. 8 is a sectional view for explaining that a fixture integrally manufactured with an abutment is coupled to the fixture holder of FIG. 6.

Referring to FIGS. 6 through 8, a dental implant package according to another embodiment of the present invention will be described. In the following description, the same structures and operations as those in the above-described embodiment will be omitted and only different structures and operations will be described.

FIG. 6 is an exploded perspective view of a dental implant package according to another embodiment of the present invention. FIG. 7 is a sectional view for explaining that a fixture where a mount is installed is coupled to a fixture holder of FIG. 6. FIG. 8 is a sectional view for explaining that a fixture integrally manufactured with an abutment is coupled to the fixture holder of FIG. 6.

As shown in FIGS. 6 through 8, a dental implant package 1a according to the present embodiment includes a fixture holder 70 instead of the leveler 40 of the above-described embodiment. The fixture holder 70, as shown in FIG. 6, includes a hollow cylinder portion 71 having a hollow shape, an arc support portion 73 having an arc (almost semi-circular) shape and extending upwardly from the hollow cylinder portion 71, and a grip portion 75 coupled to the inner circumferential wall of the arc support portion 73 to grip a fixture 3a (please refer to FIG. 7) that is inserted in and coupled to the arc support portion 73.

In the arc support portion 73, a screw portion of the fixture 3a, that is, a portion that is transplanted in an alveolar bone, does not contact the inner surface of the fixture holder 70 made of plastic. In FIG. 7, since the grip portion 75 grips the mount 6 in a state of slightly deviating from the arc support portion 73 when the mount 6 used for the transplantation of the fixture 3a is mounted on the fixture 3a, the fixture 3a coupled to the mount 6 can be supported without directly contacting the inner surface of the fixture holder 70.

In FIG. 8, a fixture 3b is integrally formed with an abutment 7. The grip portion 75 grips the abutment 7 so that the fixture 3b to be transplanted in an alveolar bone can be supported without directly contacting the inner surface of the fixture holder 70. Since the fixtures 3a and 3b supported by the fixture holder 70 are not merely the fixture 3 of FIG. 4 but the fixture 3a or 3b having the mount 6 mounted thereon or integrally formed with the abutment 7, as shown in FIGS. 7 and 8, the fixtures 3a and 3b are coupled to protrude toward the first opening 12 from the arc support portion 73. Due to this structure, the inner wall of a first cover 50a does not have the fixture push portion 52 unlike the first cover 50 where the fixture push portion 52 of FIG. 3 is provided.

As described above, the dental implant package 1a according to the present embodiment includes the fixture holder 70 that does not contact the screw portion of the fixtures 3a and 3b in supporting the fixtures 3a and 3b, so that the fixtures 3a and 3b can be stably stored and the intrusion of the external foreign materials can be prevented.

In the above-described embodiments, although the cover screw 5 is described to be stored in the auxiliary accommodation space 21, other parts such as a healing abutment used for an implant operation can be stored.

While this invention has been particularly shown and described with reference to preferred embodiments thereof, it will be understood by those skilled in the art that various changes in form and details may be made therein without departing from the spirit and scope of the invention as defined by the appended claims.

INDUSTRIAL APPLICABILITY

According to the present invention, the fixture and any of the healing abutment and the cover screw can be stored with a simple structure. Also, the fixture and the healing abutment or the cover screw can be easily pulled out during an implant operation.

What is claimed is:

1. A dental implant package comprising:
   a main body having a partition portion that is formed therein and separates a fixture accommodation space accommodating a fixture of a dental implant from an auxiliary accommodation space accommodating any of a healing abutment and a cover screw, wherein a first opening and a second opening are formed at both ends of the main body;
   a leveler accommodated in at least a part of the fixture accommodation space and supporting the fixture accommodated in the fixture accommodation space at a predetermined height;
   a first cover detachably coupled to the main body and blocking the first opening; and
   a second cover detachably coupled to the main body and blocking the second opening.

2. The dental implant package of claim 1, wherein an accommodation protrusion protruding from a lower surface in a lower end of the leveler and an accommodation hole to which the accommodation protrusion is forcibly coupled is formed at a side of the partition portion facing the leveler.

3. The dental implant package of claim 1, wherein an insertion accommodation hole in which any of the healing abutment and the cover screw is at least partially inserted is formed at the partition portion toward the auxiliary accommodation space.

4. The dental implant package of claim 3, wherein the insertion accommodation hole is formed by a hollow cylinder provided by extending from the partition portion and the accommodation hole and the insertion accommodation hole are connected to each other.

5. The dental implant package of claim 1, wherein the leveler has a cylindrical shape having an open upper end portion and a leveler cover formed of a titanium material is coupled to the upper end portion of the leveler.

6. The dental implant package of claim 1, further comprising a protection ring formed of a titanium material and coupled to an end portion of the main body forming the first opening.

7. The dental implant package of claim 1, wherein a push protrusion protruding from an outer circumferential wall of the first cover in a radial direction is provided at the first cover.

8. The dental implant package of claim 1, wherein a fixture push portion pushing the fixture when the fixture is coupled to the main body is provided on an upper surface of an inner wall of the first cover.

9. The dental implant package of claim 1, wherein a push uneven portion having an uneven shape is formed at least a part of an outer circumferential wall of the second cover.

10. A dental implant package comprising:
    a main body having a partition portion that is formed therein and separates a fixture accommodation space accommodating a fixture of a dental implant from an auxiliary accommodation space accommodating any of a healing abutment and a cover screw, wherein a first opening and a second opening are formed at both ends of the main body;
    a fixture holder accommodated in at least a part of the fixture accommodation space and supporting the fixture accommodated in the fixture accommodation space;
    a first cover detachably coupled to the main body and blocking the first opening; and
    a second cover detachably coupled to the main body and blocking the second opening.

11. The dental implant package of claim 10, wherein the fixture holder comprises:
    a hollow cylinder portion having a hollow shape;
    an arc support portion having an arc sectional shape and extending upwardly from the hollow cylinder portion; and
    a grip portion coupled to an inner circumferential wall of the arc support portion and gripping the fixture inserted and accommodated in the arc support portion.

12. The dental implant package of claim 10, wherein an insertion accommodation hole in which any of the healing abutment and the cover screw is at least partially inserted is formed at the partition portion toward the auxiliary accommodation space.

13. The dental implant package of claim 12, wherein the insertion accommodation hole is formed by a hollow cylinder provided by extending from the partition portion and the accommodation hole and the insertion accommodation hole are connected to each other.

14. The dental implant package of claim 10, wherein a push protrusion protruding from an outer circumferential wall of the first cover in a radial direction is provided at the first cover.

15. The dental implant package of claim 10, wherein a push uneven portion having an uneven shape is formed at least a part of an outer circumferential wall of the second cover.

* * * * *